(12) United States Patent
Duncan et al.

(10) Patent No.: US 12,018,094 B2
(45) Date of Patent: Jun. 25, 2024

(54) CRYSTALLINE DIPEPTIDES USEFUL IN THE SYNTHESIS OF ELAMIPRETIDE

(71) Applicant: Stealth BioTherapeutics Inc., Needham, MA (US)

(72) Inventors: Scott M. Duncan, Bedford, MA (US); Martin P. Redmon, Boston, MA (US)

(73) Assignee: Stealth BioTherapeutics Inc., Needham, MA (US)

( * ) Notice: Subject to any disclaimer, the term of this patent is extended or adjusted under 35 U.S.C. 154(b) by 0 days.

(21) Appl. No.: 18/086,203

(22) Filed: Dec. 21, 2022

(65) Prior Publication Data

US 2023/0203093 A1 Jun. 29, 2023

Related U.S. Application Data

(60) Continuation of application No. 17/224,353, filed on Apr. 7, 2021, now Pat. No. 11,560,404, which is a division of application No. 16/485,369, filed as application No. PCT/US2019/024617 on Mar. 28, 2019, now Pat. No. 10,975,118.

(60) Provisional application No. 62/651,430, filed on Apr. 2, 2018.

(51) Int. Cl.
*C07K 5/072* (2006.01)
*C07C 237/20* (2006.01)
*C07K 5/068* (2006.01)

(52) U.S. Cl.
CPC ........ *C07K 5/06095* (2013.01); *C07C 237/20* (2013.01); *C07K 5/06086* (2013.01); *C07B 2200/13* (2013.01)

(58) Field of Classification Search
CPC ............ C07B 2200/13; C07K 5/06086; C07K 5/06095; C07K 5/1019; C07C 237/20
See application file for complete search history.

(56) References Cited

U.S. PATENT DOCUMENTS

| 10,975,118 | B2 | 4/2021 | Duncan et al. |
| 11,560,404 | B2 | 1/2023 | Duncan et al. |
| 2017/0152289 | A1 | 6/2017 | Zhao et al. |
| 2019/0202861 | A1 | 7/2019 | Duncan et al. |
| 2020/0283476 | A1 | 9/2020 | Duncan et al. |
| 2021/0292274 | A1 | 9/2021 | Duncan et al. |

FOREIGN PATENT DOCUMENTS

| WO | WO2016/144905 | * | 9/2016 |
| WO | WO-2016/144905 A1 | | 9/2016 |
| WO | WO-2017/156403 A1 | | 9/2017 |
| WO | WO-2018/034901 A1 | | 2/2018 |
| WO | WO-2018/187400 A1 | | 10/2018 |
| WO | WO-2019/195080 A1 | | 10/2019 |

OTHER PUBLICATIONS

Extended European Search Report for EP Application No. 19781432.0 dated Nov. 12, 2021.
Gregory et al., "Polypeptides. Part VIII. Variations of the aspartyl position in the C-terminal tetrapeptide amide sequence of the gastrins," Journal of the Chemical Society C: Organic: 715-725 (1968).
International Search Report for International Application No. PCT/US2019/24617 dated Aug. 2, 2019.
Extended European Search Report for EP Application No. 23156906.2 dated Jul. 10, 2023.

* cited by examiner

*Primary Examiner* — Yevgeny Valenrod
*Assistant Examiner* — Blaine G Doletski
(74) *Attorney, Agent, or Firm* — Foley Hoag LLP; Dana M. Gordon (57) ABSTRACT

Disclosed are crystalline forms of L-Lys(Boc)-Phe-NH$_2$ and Boc-D-Arg-DMT. The crystalline forms may be used in the synthesis of elamipretide.

19 Claims, 2 Drawing Sheets

CRYSTALLINE DIPEPTIDES USEFUL IN THE SYNTHESIS OF ELAMIPRETIDE

RELATED APPLICATIONS

This application is a continuation of U.S. patent application Ser. No. 17/224,353, filed Apr. 7, 2021; which is a divisional of U.S. patent application Ser. No. 16/485,369, filed Aug. 12, 2019, now U.S. Pat. No. 10,975,118; which is the U.S. National Stage of PCT/US19/24617, filed Mar. 28, 2019; which claims the benefit of priority to U.S. Provisional Patent Application No. 62/651,430, filed Apr. 2, 2018.

BACKGROUND OF THE INVENTION

Elamipretide (MTP-131) is a mitochondria-targeting peptide compound with therapeutic potential for treating diseases associated with mitochondrial dysfunction. Elamipretide contains four-amino acid residues and has been synthesized according to typical linear and convergent solution phase peptide synthesis methods. The synthetic routes to generate elamipretide that have been used to date require the preparation of various differentially protected peptides, such that certain protecting groups are selectively removed in order to subject the deprotected compound to peptide coupling, while other protecting groups remain to prevent unwanted side reactions. Even with protecting groups such coupling reactions and related steps generate impurities. Thus, there exists a need to develop new methods to purify elamipretide that allow the purification after coupling reactions. Crystallization of the desired reaction products are one method of achieving the necessary purification.

SUMMARY OF THE INVENTION

Disclosed are crystalline forms of L-Lys(Boc)-Phe-NH$_2$ and Boc-D-Arg-DMT, wherein DMT is an abbreviation for dimethyltyrosine, which are intermediates in the synthesis of elamipretide.

DETAILED DESCRIPTION OF THE INVENTION

Elamipretide has been shown to have various therapeutic effects in diseases related to mitochondrial dysfunction. Previous synthetic routes to elamipretide presented challenges with respect to scale-up due to reliance on chromatographic separations to enrich levels of desired intermediates. Herein are disclosed crystalline forms of L-Lys(Boc)-Phe-NH$_2$ and Boc-D-Arg-DMT, which can be used as purified intermediates in the synthesis of elamipretide.

One aspect of the present invention relates to crystalline forms of Compound (I):

(I)

which compound is also known as L-Lys(Boc)-Phe-NH$_2$.

A crystalline form of Compound (I) can be used in the synthesis of elamipretide.

In certain embodiments, a polymorph of the crystalline form is characterized by powder X-ray diffraction (XRD). θ represents the diffraction angle, measured in degrees. In certain embodiments, the diffractometer used in XRD measures the diffraction angle as two times the diffraction angle θ. Thus, in certain embodiments, the diffraction patterns described herein refer to X-ray intensity measured against angle 2θ.

In certain embodiments, a crystalline form of Compound (I) is not solvated (e.g., the crystal lattice does not comprise molecules of a solvent). In certain alternative embodiments, a crystalline form of Compound (I) is solvated. In some cases, the solvent is water.

Figure 1:
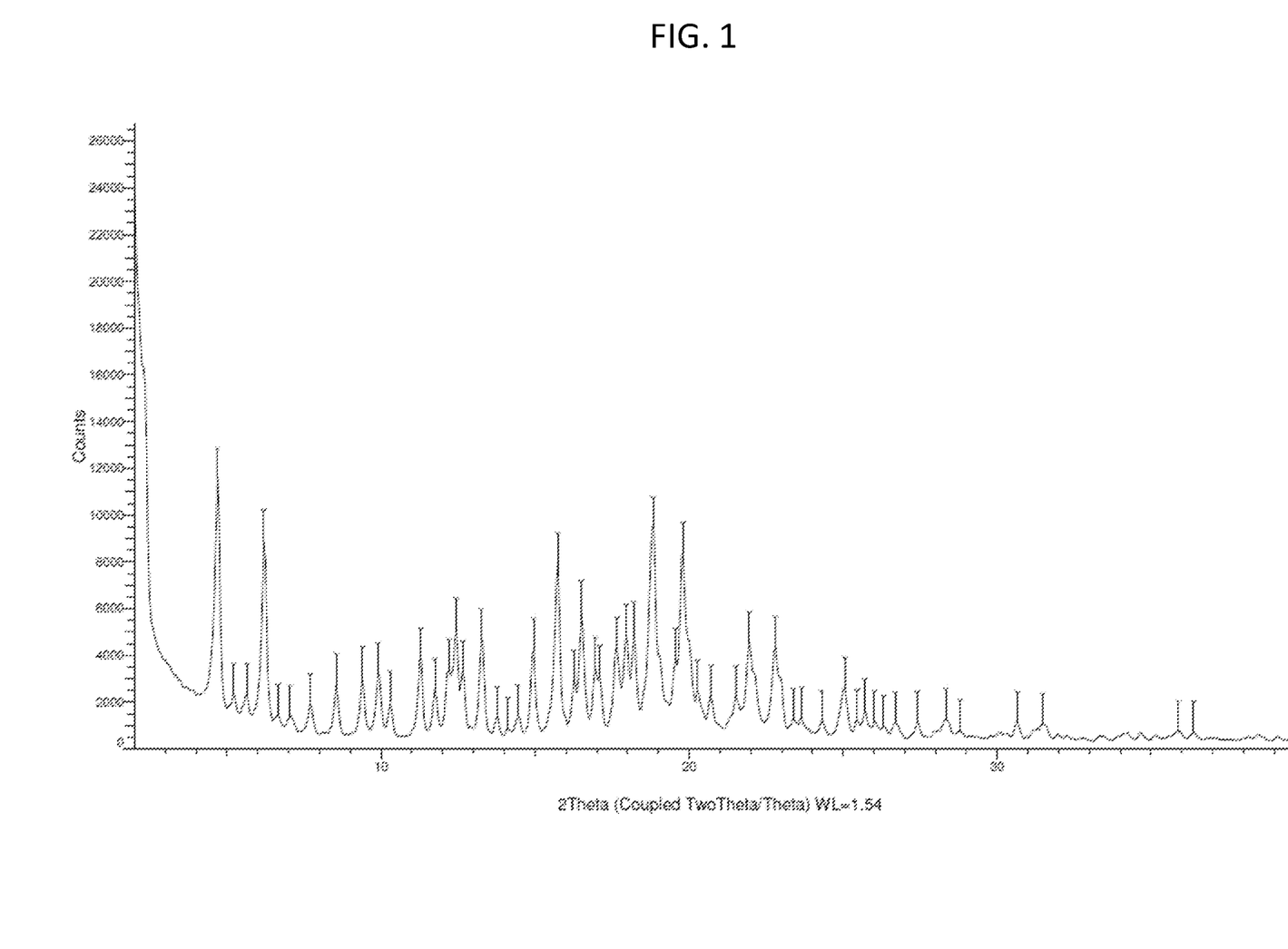
FIG. 1 is the XRPD pattern of crystalline L-Lys(Boc)-Phe-NH$_2$. The peak listing of the XRPD pattern depicted in FIG. 1 is described in Table 1.

In one aspect, the invention features a crystalline form of Compound (I) which has characteristic peaks in the powder X-ray diffraction (XRPD) pattern as shown in FIG. 1.

In another aspect, the invention features a crystalline form of Compound (I) which has characteristic peaks in the powder X-ray diffraction (XRPD) pattern at values of two theta (° 2θ) as shown in Table 1.

In another aspect, the invention features a crystalline form of Compound (I) which has characteristic peaks in the powder X-ray diffraction (XRPD) pattern at values of two theta (° 2θ) of: 4.7, 6.2, 12.4, 15.8, 16.5, 18.0, 18.2, 18.8, and 19.8.

In another aspect, the invention features a crystalline form of Compound (I) which has characteristic peaks in the powder X-ray diffraction (XRPD) pattern at values of two theta (° 2θ) of: 4.7, 6.2, 11.3, 12.4, 13.3, 15.0, 15.8, 16.5, 17.0, 17.7, 18.0, 18.2, 18.8, 19.8, 22.0, and 22.8.

The relative intensity, as well as the two theta value, of each peak in Table 1, as well as in FIG. 1, may change or shift under certain conditions, although the crystalline form is the same. One of ordinary skill in the art should be able to determine readily whether a given crystalline form is the same crystalline form as described in Table 1, as well as in FIG. 1, by comparing their XRPD data.

One aspect of the present invention relates to a crystalline form of Compound (II):

(II)

which compound is also known as Boc-D-Arg-DMT, and may also be drawn in the form of a zwitterion.

A crystalline form of Compound (II) can be used in the synthesis of elamipretide.

In certain embodiments, a polymorph of the crystalline form is characterized by powder X-ray diffraction (XRD). θ represents the diffraction angle, measured in degrees. In certain embodiments, the diffractometer used in XRD measures the diffraction angle as two times the diffraction angle θ. Thus, in certain embodiments, the diffraction patterns described herein refer to X-ray intensity measured against angle 2θ.

In certain embodiments, a crystalline form of Compound (II) is not solvated (e.g., the crystal lattice does not comprise molecules of a solvent). In certain alternative embodiments, a crystalline form of Compound (II) is solvated. In some cases, the solvent is water.

Figure 2:
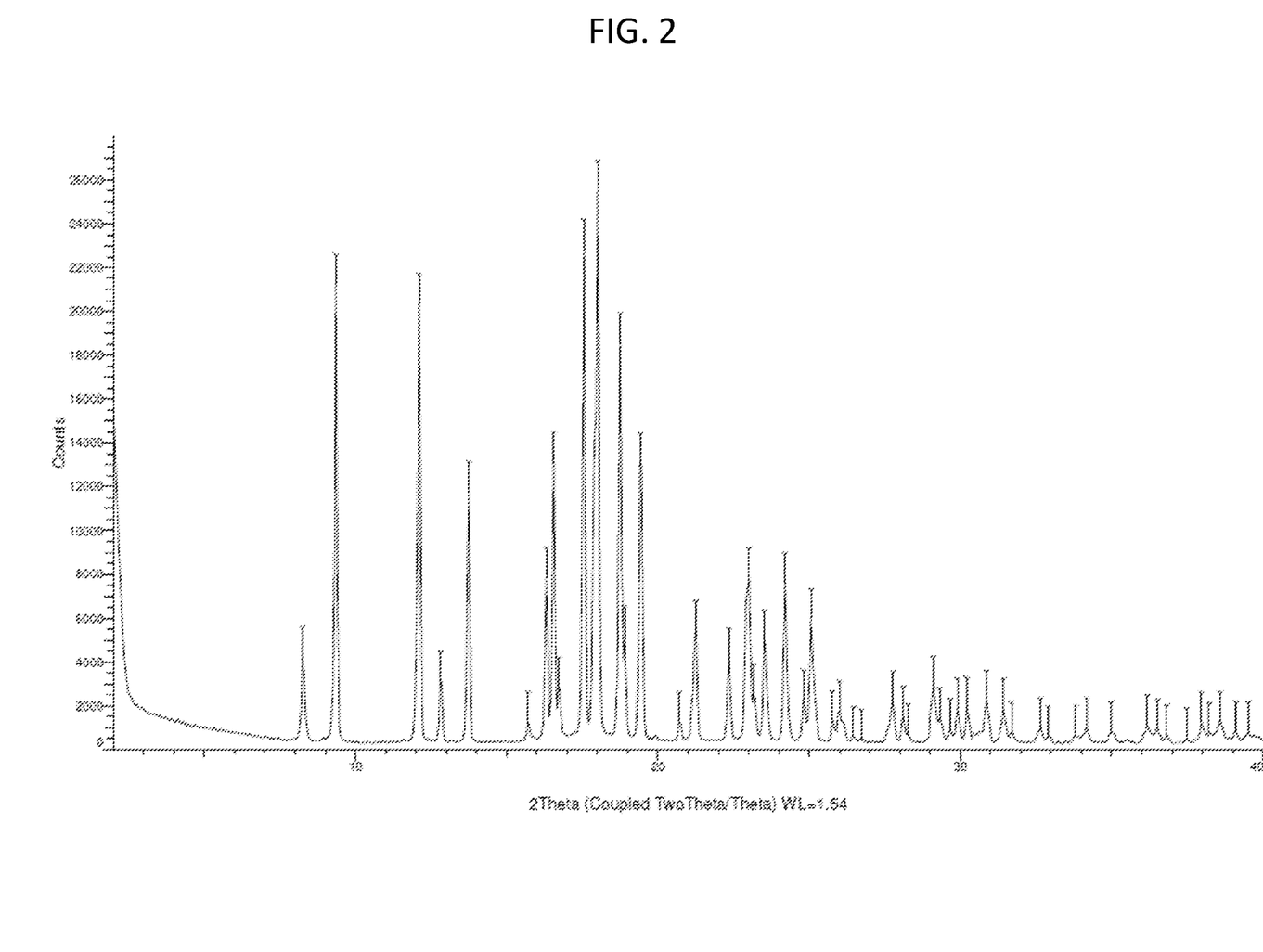
FIG. 2 is the XRPD pattern crystalline Boc-D-Arg-DMT. The peak listing of the XRPD pattern depicted in FIG. 2 is described in Table 2.

In one aspect, the invention features a crystalline form of Compound (II) which has characteristic peaks in the powder X-ray diffraction (XRPD) pattern as shown in FIG. 2.

In another aspect, the invention features a crystalline form of Compound (II) which has characteristic peaks in the powder X-ray diffraction (XRPD) pattern at values of two theta (° 2θ) as shown in Table 2.

In another aspect, the invention features a crystalline form of Compound (II) which has characteristic peaks in the powder X-ray diffraction (XRPD) pattern at values of two theta (° 2θ) of: 9.3, 12.1, 16.6, 17.6, 18.0, 18.8, and 19.4.

In another aspect, the invention features a crystalline form of Compound (II) which has characteristic peaks in the powder X-ray diffraction (XRPD) pattern at values of two theta (° 2θ) of: 9.3, 12.1, 13.7, 16.3, 16.6, 17.6, 18.0, 18.8, 19.4, 21.3, 23.0, 24.2, and 25.1.

The relative intensity, as well as the two theta value, of each peak in Table 2, as well as in FIG. 2, may change or shift under certain conditions, although the crystalline form is the same. One of ordinary skill in the art should be able to determine readily whether a given crystalline form is the same crystalline form as described in Table 1, as well as in FIG. 1, by comparing their XRPD data.

EXAMPLES

Materials and Methods

| Name | RM0858 General Method (2607) |
|---|---|
| Parent | 2Theta |
| Sample Name | S-18-0011882 SCC-169 |
| File Name | RM0858 General Method (2607) |
| Scan Type | Coupled TwoTheta/Theta |
| Scan Mode | Continuous PSD fast |
| Start | 2.000 |
| End | 40.016 |
| Step Size | 0.050 |
| Time per Step | 192.00 |
| Anode | Cu |
| kα1 | 1.54 |
| Generator kV | 40.0 |
| Generator mA | 40.0 |
| PSD Opening | 2.940 |
| Detector Slit Opening | |
| Primary Soller slit | 2.500 |
| Secondary Soller slit | 2.500 |
| Sample rotation speed | 15.000 |
| Divergence Slit | 0.600 |
| Antiscatter Slit | 3.000 |
| Slit Mode | Fixed |

Example 1. L-Lys(Boc)-Phe-NH$_2$ (Compound I)

Exemplary Synthetic Route

1
Chemical Formula:
C$_9$H$_{13}$ClN$_2$O
Molecular Weight: 200.67
Phe-NH$_2$—HCl 2
Chemical Formula:
C$_{19}$H$_{28}$N$_2$O$_6$
Molecular Weight: 380.44
Cbz-Lys(Boc)

3
Chemical Formula:
C$_{28}$H$_{38}$N$_4$O$_6$
Molecular Weight: 526.63
Cbz-Lys(Boc)-Phe-NH2

I
Chemical Formula:
C$_{20}$H$_{32}$N$_4$O$_4$
Molecular Weight: 392.50
Lys(Boc)-Phe-NH2

| | Operation | Charge | Units |
|---|---|---|---|
| | Inert the reactor with nitrogen. | | |
| 1 | Charge Compound 1 to reactor. | 950.00 | g |
| 2 | Charge Compound 2 to reactor. | 1891.11 | g |
| 3 | Charge HOBt-H2O to reactor. | 797.48 | g |
| 4 | Charge DMAc to reactor. | 3736.49 | g |
| 5 | Adjust solution to target 22° C. (19 to 25° C.) with agitation. | | |
| 6 | Agitate for 10-15 min at 22° C. (19 to 25° C.). | | |
| 7 | Slowly charge NMM to reactor with moderate agitation. | 957.72 | g |
| 8 | Adjust solution to target 7° C. (4 to 10° C.) with agitation. | | |
| 9 | Slowly charge EDCI to reactor with vigorous agitation. | 952.91 | g |
| 10 | Adjust solution to target 7° C. (4 to 10° C.) with vigorous agitation. | | |
| 11 | Charge EtOH to reactor with vigorous agitation. | 750.50 | g |
| 12 | Adjust solution to target 22° C. (19 to 25° C.) with vigorous agitation. | | |
| 13 | Agitate vigorously for ≥1 h at 22° C. (19 to 25° C.). | | |
| | IPC for Reaction Completion (≤1.0% Phe-NH2 remaining) | 0.169% | a/a |
| | CRYSTALLIZATION | | |
| 15 | Charge ACN to the reactor with vigorous agitation. | 11202.70 | g |
| 16 | Agitate vigorously for ≥5 h at 22° C. (19 to 25° C.). | | |
| 17 | Verify crystallization successful. | | |
| 18 | Filter the reaction to isolate the product (SCC-175). | | |
| 19 | Wash the product cake with ACN and combine with mother liquor. | 11202.70 | g |
| 20 | Dry the product with agitation and nitrogen bleed for at least 17 h. | | |

Synthesis of Compound 3

| Name | Amount (g) | Volume (mL) | MW (g/mol) | Molar Equiv | Moles | Density g/mL | BR Charge Amt (kg) | kg/kg |
|---|---|---|---|---|---|---|---|---|
| Phe-NH2 HCl | 950.00 | 950.00 | 200.67 | 1.00 | 4.734 | — | 7.030 | |
| Cbz-Lys(Boc)-OH | 1891.11 | 1891.11 | 380.44 | 1.05 | 4.971 | — | 13.990 | 1.99 |
| HOBt-H$_2$O | 797.48 | 797.48 | 153.14 | 1.10 | 5.208 | — | 5.900 | 0.84 |
| Dimethylacetamide (DMAc) | 3736.49 | 3987.71 | 87.12 | — | — | 0.937 | 27.650 | 3.93 |
| N-Methylmorpholine (NMM) | 957.72 | 1041.00 | 101.15 | 2.00 | 9.468 | 0.920 | 7.080 | 1.01 |
| EDCI | 952.91 | 952.91 | 191.70 | 1.05 | 4.971 | — | 7.050 | 1.00 |
| Anhydrous Ethyl Alcohol (EtOH) | 750.50 | 951.20 | 46.07 | — | — | 0.789 | 5.550 | 0.79 |
| Acetonitrile (ACN) | 11202.70 | 14252.80 | 84.93 | — | — | 0.786 | 82.900 | 11.79 |
| Acetonitrile (ACN) | 11202.70 | 14252.80 | 85.93 | — | — | 0.786 | 82.900 | 11.79 |

Synthesis of Compound I

| Name | Amt | Volume (mL) | MW (g/mol) | Molar Equiv | Density g/mL | BR Charge Amt | units | kg/kg |
|---|---|---|---|---|---|---|---|---|
| Compound 3 | 2000.00 | 2000.00 | 526.63 | 1.00 | | 15.700 | kg | |
| 10% Pd/C (50% w/w wet) | 200.00 | 200.00 | 106.42 | 10% w/w | — | 3.140 | kg | 0.20 |
| Anhydrous Methyl Alcohol (MeOH) | 14191.08 | 17918.03 | 32.04 | — | 0.792 | 111.400 | kg | 7.10 |
| Anhydrous Methyl Alcohol (MeOH) | 7000.00 | 8838.38 | 32.04 | — | 0.792 | 54.950 | kg | 3.50 |
| Water | 7000.00 | 7000.00 | 18.02 | | 1.000 | 54.950 | kg | 3.50 |
| Water | 8000.00 | 8000.00 | 18.02 | | 1.000 | 62.800 | kg | 4.00 |
| MeOH-Water (1:9) Solution | 8000.00 | 7896.00 | | | 0.987 | 62.800 | kg | 4.00 |
| Water (1:9 MeOH-water make-up) | 9000.00 | 9000.00 | 18.02 | | 1.000 | NA | | NA |
| Anhydrous Methyl Alcohol (MeOH) (1:9 MeOH-water make-up) | 792.00 | 1000.00 | 33.04 | — | 0.792 | NA | | NA |

| | Operation | Charge | Units |
|---|---|---|---|
| | REACTION (30 L Hydrogenator Main Reactor) | | |
| 1 | Inert the hydrogenation reactor with nitrogen. Charge Pd/C (10%, 50% w/w water, 20A597) to reactor. | 200.00 | g |
| 2 | Charge Compound 3 to reactor. | 2000.00 | g |
| 3 | Charge MeOH to the reactor. | 14191.08 | g |
| 4 | Adjust solution to target 22° C. (19 to 25° C.) with agitation. Inert the hydrogenation reactor with nitrogen. | | |
| 5 | Pressurize the reactor with hydrogen (20-25 psi). | | |
| 6 | Agitate for ≥6 h at 22° C. (19 to 25° C.) and 20-25 psi hydrogen. Note: Maintain the pressure at 20-25 psi hydrogen. | | |
| 7 | De-pressurize the reactor and inert with nitrogen at 22° C. (19 to 25° C.). | | |
| | IPC for Reaction Completion (≤0.5% SCC-175 remaining) | 0.09% | a/a |
| 9 | Filter the reaction to remove catalyst. | | |
| 10 | Rinse the filter cake with MeOH and combine with filtrate. | 7000.00 | g |
| | DISTILLATION (30 L ChemGlass Jacketed Main Reactor) | | |
| 11 | Distill the reaction at ≤45° C. (100-200 Torr vacuum) to target. Note: Distillation target = 1.5-2.5 mL/g SCC-175 charge. | 5000.00 | mL |
| | PRECIPITATION (30 L ChemGlass Jacketed Main Reactor) | | |
| | ISOLATION (12 L Allen Glass Filter w/30 micron ChemGlass teflon frit) | | |
| 12 | Charge water to reactor with moderate agitation at 40° C. over 30-60 min. | 7000.00 | g |
| 13 | Agitate the reaction at 40° C. until crystallization observed. | | |
| 14 | Verify crystallization successful. | | |
| 15 | Charge water to reactor with moderate agitation at 40° C. over 30-60 min. | 8000.00 | g |
| 16 | Adjust the reaction to 22° C. (20 to 25° C.) over 30-60 min. | | |
| 17 | Filter the reaction to isolate the product (SCC-169). | | |
| 18 | Wash the product cake with MeOH-water (1:9). | 8000.00 | g |
| 19 | Dry the product with agitation and nitrogen bleed for at least 17 h. | | |

Preliminary Single-Solvent Solubility of Compound I:

| Solvent | Solubility (mg/mL)[A] |
|---|---|
| EtOH (SDAG-7) | 154.8 |
| THF | 84.5 |
| iPrOAc | 5.1 |
| MeOAc | 18.2 |
| Water | 4.1 |

[A]Solubility was determined by HPLC (response curve).

Preliminary Precipitation Studies (MeOH/Water) of Compound I:

| | | Precipitation Studies | | | |
|---|---|---|---|---|---|
| Experiment | MeOH/ Water | Addition Mode | Precip (Y/N) | Concentration (mL/g) | Solubility (mg/mL) |
| 1[A] | 1:3 | Normal | Y | 10 | 7.0 |
| 2[A] | 1:5 | Normal | Y | 10 | 5.0 |
| 3[A] | 1:9 | Normal | Y | 10 | 3.6 |
| 4[A] | 1:19 | Normal | Y | 10 | 2.7 |
| 5[B] | 1:3 | Reverse | N | 80 | — |

-continued

Precipitation Studies

| Experiment | MeOH/ Water | Addition Mode | Precip (Y/N) | Concentration (mL/g) | Solubility (mg/mL) |
|---|---|---|---|---|---|
| +2 parts water | 1:5 | Normal | Y | 120 | ND |

[A]Experiments were conducted on 500 mg scale where the initial solution in MeOH (via 2447-41) was concentrated to a residue followed by charging MeOH/water at 25° C.

[B]Experiment was conducted on 40 mg scale where the initial solution in MeOH (via 2447-41) was charged directly to water. An additional charge of water was required to enable precipitation.

In Process Precipitation Results (MeOH/Water) of Compound I:

Precipitation Results

| Experiment | MeOH/Water | Concentration (mL/g) | Solubility (mg/mL) | Total Losses |
|---|---|---|---|---|
| 2447-41[A] | 1:9 | 13 | 2.5 | 5.7% |
| 2447-47[A] | 1:5 | 10 | 4.2 | 6.2% |

Example 2. Boc-D-Arg-DMT-OH

6
$C_{18}H_{22}ClNO_3$
335.83
DMT-OBn HCl

+

7
$C_{11}H_{23}ClN_4O_4$
310.78
Boc-D-Arg HCl

8
$C_{29}H_{42}ClN_5O_6$
592.13
Boc-D-Arg-DMT-OBn-HCl

II
$C_{22}H_{36}ClN_5O_6$
502.01
Boc-D-Arg-DMT-HCl

Manufacturing Process to Produce Compound 8

| Step | Operation |
|---|---|
| 1 | Charge DMT-OBn HCl (1 eq) and Boc-D-Arg-OH HCl (1.05 eq) to the reactor. |
| 2 | Charge HOBt (0.1 eq) and DCM (8.5 L/kg of DMT-OBn HCl) to the reactor. |
| 3 | Adjust temperature to about 22 ± 3° C. and charge NMM (2.0 eq) to the reactor |
| 4 | Adjust temperature to about 15 ± 3° C. and charge EDCI (1.05 eq) to the reactor. |
| 5 | Adjust temperature to about 15° C. and agitate. |
| 5 | Charge EtOH (1.5 L/kg of DMT-OBn HCl) to the reactor |
| 7 | Agitate for a minimum of 5 hours at 15 ± 3° C. |
| 8 | Sample for in-process control reaction completion test, if reaction is not complete, charge additional EDCI, stir for a minimum of 1 hour andrepeat the in-process control test until criterion for completion is met. |
| 9 | Charge 15% EtOH in DCM. |
| 10 | Charge 1M HCl. |
| 11 | Adjust temperature to ambient and agitate. |
| 12 | Stop agitation and separate layers |
| 13 | Wash organic layer successively with brine, 1M HCl, brine and then brine again |
| 14 | Reduce volume via vacuum distillation |

| Step | Operation |
|---|---|
| 15 | Adjust temperature to ambient |
| 16 | Charge EtOH and reduce volume via vacuum distillation |
| 17 | Sample for in-process control DCM content test, Repeat EtOH addition and volume reduction by vacuum distillation until the in-process control limit for DCM is met |
| 18 | Adjust temperature to ambient |
| 19 | Sample the product for in-process control test for SCC-192 purity and content |

Manufacturing Process to Produce the HCl salt of Compound II

| Step | Operation |
|---|---|
| 1 | Charge the ethanol solution of Boc-D-Arg-DMT-OBn HCl (SCC-192) |
| 2 | Charge 10% Pd/C, 50% wet (w/w) (20 wt. %) |
| 3 | Charge EtOH (7 L/kg of SCC-192) |
| 4 | Agitate and begin hydrogenation around ambient temperature |
| 5 | Step 2B In-Process Control 1: Test for reaction completion |
| 5 | Filter suspension through filter aid and wash filter cake three times with EtOH |
| 7 | Reduce volume via vacuum distillation |
| 8 | Adjust temperature to ambient |
| 9 | Charge THF and reduce volume via vacuum distillation |
| 10 | Adjust temperature to ambient |
| 11 | Charge THF and reduce volume via vacuum distillation |
| 12 | Adjust temperature to ambient |
| 13 | Charge THF and reduce volume via vacuum distillation |
| 14 | Step 2B In-Process Control 2: Test for EtOH content |
| 15 | Charge iPrOAc and agitate at ambient temperature |
| 16 | Filter and wash solids three times with iPrOAc |
| 17 | Dry the product under vacuum and nitrogen |
| 18 | Sample the product for in-process control test for purity |
| 19 | Step 2B In-Process Control 3: Test for Purity |

Preparation of the Zwitterionic Form of Compound II $C_{22}H_{36}ClN_5O_6$
502.0090
Boc-D-Arg-DMT·HCl $C_{22}H_{35}N_5O_6$
465.5510
Boc-D-Arg(H$^+$)-DMT-O$^-$ 1. The crude HCl salt is suspended in $CH_3OH/H_2O$ (1/1, v/v)
2. The suspension is heated to 45-50° C.
3. After the clear solution is formed, an aqueous solution of $Na_2CO_3$ (1.2 eq.) is added. During the addition, the solid begins to precipitate.
4. The suspension is stirred for 1 h at 45° C., and then cooled to 15° C. and stirred for an additional hour.
5. The solid is isolated by filtration and dried to provide Compound II with high purity (99.4 area %) by HPLC. The calculated w/w assay correcting for residual solvents, water content and residue on ignition for this demonstration run was 98.7%.

Formation of zwitterionic compound led to high purity material that was stable, easily handled, and highly crystalline.

Example 3. Crystalline
L-Lys(Boc)-Phe-NH$_2$—XRPD Peak List (Table 1)

| Angle | d Value | Net Intensity | Gross Intensity | Rel. Intensity |
|---|---|---|---|---|
| 4.704 | 18.77211 | 9559 | 11528 | 100.0% |
| 5.230 | 16.88407 | 624 | 2301 | 6.5% |
| 5.648 | 15.63394 | 862 | 2340 | 9.0% |
| 6.200 | 14.24402 | 7663 | 8912 | 80.2% |
| 6.650 | 13.28067 | 394 | 1456 | 4.1% |
| 7.056 | 12.51772 | 508 | 1400 | 5.3% |
| 7.709 | 11.45860 | 1161 | 1869 | 12.1% |
| 8.553 | 10.33046 | 2135 | 2771 | 22.3% |
| 9.402 | 9.39869 | 2473 | 3073 | 25.9% |
| 9.922 | 8.90729 | 2627 | 3206 | 27.5% |
| 10.303 | 8.57920 | 1435 | 1997 | 15.0% |
| 11.292 | 7.82975 | 3301 | 3848 | 34.5% |
| 11.755 | 7.52244 | 1985 | 2530 | 20.8% |
| 12.265 | 7.24594 | 2827 | 3370 | 29.6% |
| 12.452 | 7.10258 | 4581 | 5123 | 47.9% |
| 12.655 | 6.98916 | 2764 | 3305 | 28.9% |
| 13.270 | 6.66655 | 4117 | 4655 | 43.1% |
| 13.778 | 6.42221 | 795 | 1330 | 8.3% |
| 14.133 | 6.26164 | 333 | 866 | 3.5% |
| 14.462 | 6.11961 | 882 | 1413 | 9.2% |
| 14.957 | 5.91833 | 3726 | 4255 | 39.0% |
| 15.756 | 5.61997 | 7404 | 7928 | 77.5% |
| 16.263 | 5.44580 | 2360 | 2881 | 24.7% |
| 16.504 | 5.36683 | 5366 | 5885 | 56.1% |
| 16.961 | 5.22337 | 2930 | 3447 | 30.7% |

| Angle | d Value | Net Intensity | Gross Intensity | Rel. Intensity |
|---|---|---|---|---|
| 17.107 | 5.17917 | 2585 | 3100 | 27.0% |
| 17.658 | 5.01859 | 3807 | 4320 | 39.8% |
| 17.956 | 4.93596 | 4360 | 4871 | 45.6% |
| 18.210 | 4.86777 | 4451 | 4960 | 46.6% |
| 18.832 | 4.70852 | 8963 | 9468 | 93.8% |
| 19.561 | 4.53460 | 3331 | 3830 | 34.8% |
| 19.802 | 4.47996 | 7877 | 8375 | 82.4% |
| 20.265 | 4.37865 | 1989 | 2483 | 2.8% |
| 20.715 | 4.28449 | 1746 | 2237 | 18.3% |
| 21.514 | 4.12715 | 1756 | 2241 | 18.4% |
| 21.958 | 4.04471 | 4087 | 4568 | 42.7% |
| 22.807 | 3.89590 | 3856 | 4331 | 40.3% |
| 23.398 | 3.79891 | 779 | 1248 | 8.1% |
| 23.660 | 3.75740 | 835 | 1303 | 8.7% |
| 24.306 | 3.65896 | 726 | 1188 | 7.6% |
| 25.050 | 3.55198 | 2158 | 2614 | 22.6% |
| 25.462 | 3.49548 | 764 | 1217 | 8.0% |
| 25.709 | 3.46234 | 1227 | 1677 | 12.8% |
| 26.016 | 3.42222 | 714 | 1161 | 7.5% |
| 26.319 | 3.38357 | 521 | 966 | 5.5% |
| 26.713 | 3.33445 | 662 | 1103 | 6.9% |
| 27.411 | 3.25119 | 709 | 1143 | 7.4% |
| 28.356 | 3.14493 | 831 | 1256 | 8.7% |
| 28.808 | 3.09564 | 340 | 761 | 3.6% |
| 30.662 | 2.91341 | 740 | 1142 | 7.7% |
| 61.492 | 2.83854 | 649 | 1041 | 6.8% |
| 35.876 | 2.50109 | 376 | 740 | 3.9% |
| 36.369 | 2.46832 | 362 | 723 | 3.8% |

Example 4. Crystalline Boc-D-Arg-DMT—XRPD Peak List (Table 2)

| Angle | d Value | Net Intensity | Gross Intensity | Rel. Intensity |
|---|---|---|---|---|
| 8.253 | 10.70448 | 3779 | 4204 | 15.0% |
| 9.353 | 9.44784 | 20863 | 21225 | 82.9% |
| 12.104 | 7.30592 | 20016 | 20338 | 79.6% |
| 12.809 | 6.90584 | 2797 | 3120 | 11.1% |
| 13.755 | 6.43269 | 11432 | 11758 | 45.4% |
| 15.709 | 5.53659 | 906 | 1235 | 3.6% |
| 16.307 | 5.43127 | 7500 | 7829 | 29.8% |
| 16.556 | 5.35006 | 12773 | 13103 | 50.8% |
| 16.725 | 5.29645 | 2495 | 2825 | 9.9% |
| 17.557 | 5.04740 | 22493 | 22824 | 89.4% |
| 18.006 | 4.92236 | 25154 | 25485 | 100.0% |
| 18.756 | 4.72740 | 18203 | 18534 | 72.4% |
| 18.908 | 4.68953 | 4809 | 5141 | 19.1% |
| 19.414 | 4.56848 | 12725 | 13056 | 50.6% |
| 20.715 | 4.28417 | 899 | 1231 | 3.6% |
| 21.259 | 4.17597 | 5674 | 5406 | 20.2% |
| 22.357 | 3.97329 | 3830 | 4161 | 15.2% |
| 23.009 | 3.86218 | 7511 | 7842 | 29.9% |
| 23.153 | 3.83695 | 2203 | 2533 | 8.8% |
| 23.511 | 3.78085 | 4659 | 4989 | 18.5% |
| 24.208 | 3.57354 | 7257 | 7585 | 28.8% |
| 24.809 | 3.58598 | 1940 | 2268 | 7.7% |
| 25.060 | 3.55054 | 5627 | 5954 | 22.4% |
| 25.767 | 3.45478 | 970 | 1297 | 3.9% |
| 26.009 | 3.42308 | 1418 | 1744 | 5.6% |
| 26.457 | 3.36613 | 255 | 580 | 1.0% |
| 26.721 | 3.33347 | 161 | 485 | 0.6% |
| 27.763 | 3.21973 | 1852 | 2185 | 7.4% |
| 28.111 | 3.17181 | 1182 | 1503 | 4.7% |
| 28.263 | 3.15505 | 366 | 687 | 1.5% |
| 29.111 | 3.06507 | 2546 | 2864 | 10.1% |
| 29.311 | 3.04456 | 1100 | 1418 | 4.4% |
| 29.652 | 3.00931 | 616 | 933 | 2.4% |
| 29.912 | 2.98475 | 1550 | 1865 | 6.2% |
| 30.212 | 2.95583 | 1607 | 1922 | 6.4% |
| 30.865 | 2.89475 | 1913 | 2226 | 7.6% |
| 31.414 | 2.84540 | 1565 | 1876 | 6.2% |
| 31.695 | 2.82084 | 468 | 778 | 1.9% |
| 32.665 | 2.73926 | 657 | 963 | 2.6% |
| 32.915 | 2.71901 | 296 | 602 | 1.2% |
| 33.805 | 2.64939 | 326 | 632 | 1.3% |
| 34.165 | 2.62230 | 670 | 976 | 2.7% |
| 34.977 | 2.56330 | 485 | 795 | 1.9% |
| 36.166 | 2.48167 | 798 | 1113 | 3.2% |
| 36.514 | 2.45883 | 611 | 927 | 2.4% |
| 36.813 | 2.43955 | 364 | 682 | 1.4% |
| 37.466 | 2.39651 | 173 | 502 | 0.7% |
| 37.966 | 2.36808 | 901 | 1257 | 3.6% |
| 38.221 | 2.35285 | 394 | 764 | 1.6% |
| 38.576 | 2.33202 | 878 | 1265 | 3.5% |
| 39.114 | 2.30117 | 394 | 810 | 1.6% |
| 39.516 | 2.27866 | 363 | 801 | 1.4% |

INCORPORATION BY REFERENCE

All U.S. patents and U.S. and PCT published patent applications mentioned in the description above are incorporated by reference herein in their entirety.

EQUIVALENTS

Having now fully described the present invention in some detail by way of illustration and examples for the purposes of clarity of understanding, it will be obvious to one of ordinary skill in the art that the same can be performed by modifying or changing the invention within a range of conditions, formulations and other parameters without affecting the scope of the invention or any specific embodiment thereof, and that such modifications or changes are intended to be encompassed within the scope of the appended claims.

We claim:

1. A crystalline form of a compound according to formula II:

(II)

2. A method of making a compound of formula II:

comprising:
(a) combining an HCl salt represented by formula I, and a mixture of CH₃OH and H₂O, thereby forming a suspension comprising the compound of Formula II; wherein the compound of formula I is:

3. The method of claim 2, further comprising:
(b) heating the suspension, thereby forming a solution.
4. The method of claim 3, wherein the suspension is heated to about 45° C. to about 50° C.
5. The method of claim 3, further comprising:
(c) adding an aqueous solution of Na₂CO₃ to the solution formed in (b), thereby forming a second suspension.
6. The method of claim 5, wherein about 1.2 equivalents of Na₂CO₃ is added relative to the amount of the compound of formula I.
7. The method of claim 5, further comprising:
(d) stirring the second suspension.
8. The method of claim 7, wherein the second suspension is heated to about 45° C. while being stirred.
9. The method of claim 8, wherein the second suspension is stirred at about 45° C. for about one hour.
10. The method of claim 8, further comprising:
(e) cooling the second suspension to about 15° C.
11. The method of claim 10, wherein the second suspension is stirred at about 15° C. for about one hour.

12. The method of claim 10, further comprising:
(f) isolating from the second suspension the compound of formula II in solid form.
13. The method of claim 12, wherein (f) comprises filtering the second suspension, and collecting the solid form of the compound of formula II.
14. The method of claim 13, further comprising:
(g) drying the compound of formula II, thereby forming a dried compound of formula II.
15. The method of claim 14, wherein the dried compound of formula II has a purity of 99.4% as measured by HPLC.
16. The method of claim 14, wherein the dried compound of formula II is crystalline.
17. A method of making a compound of formula II:

comprising:
(a) adding an aqueous solution of Na₂CO₃ to a solution comprising an HCl salt represented by formula I and a mixture of CH₃OH and H₂O; wherein the HCl salt of formula I is:

thereby forming a suspension comprising the compound of Formula II.
18. The method of claim 17, wherein about 1.2 equivalents of Na₂CO₃ is added relative to the amount of the compound of formula I.

19. The method of claim 17, further comprising:
(b) isolating from the suspension the compound of formula II in solid form, wherein the solid form of formula II has a purity of 99.4% as measured by HPLC.

* * * * *